United States Patent [19]

Shih et al.

[11] Patent Number: 5,077,198

[45] Date of Patent: Dec. 31, 1991

[54] DIAGNOSTIC KIT AND METHOD FOR RAPID DETECTION OF ANTIBODIES

[75] Inventors: Yihshing Shih, San Mateo, Calif.; Harold C. Warren, III, Rush; Margaret J. Smith-Lewis, Pittsford, both of N.Y.

[73] Assignee: Eastman Kodak Company, Rochester, N.Y.

[21] Appl. No.: 181,465

[22] Filed: Apr. 14, 1988

[51] Int. Cl.$^5$ ..................... C12Q 1/70; G01N 33/537
[52] U.S. Cl. ........................ 435/7.9; 435/5; 435/7.1; 435/810; 436/518; 436/534; 436/536; 436/538; 436/808
[58] Field of Search ............... 436/518, 534, 536, 538, 436/174, 177, 179, 807, 808, 809, 826; 435/5, 7, 810, 7.1, 7.9

[56] References Cited

U.S. PATENT DOCUMENTS

| | | | |
|---|---|---|---|
| 4,520,113 | 5/1985 | Gallo et al. | 436/504 |
| 4,639,425 | 1/1987 | Baier | 436/534 X |
| 4,661,445 | 4/1987 | Saxinger et al. | 435/7 |
| 4,708,818 | 11/1987 | Montagnier et al. | 435/5 |
| 4,725,669 | 2/1988 | Essex . | |
| 4,812,414 | 3/1989 | Warren, III et al. | 436/533 |
| 4,868,131 | 9/1989 | Hiratsuka | 436/538 X |
| 4,935,339 | 6/1990 | Zahradnik | 435/5 |

FOREIGN PATENT DOCUMENTS

| | | |
|---|---|---|
| 136798 | 4/1985 | European Pat. Off. . |
| 0217403 | 4/1987 | European Pat. Off. . |
| 0234941 | 9/1987 | European Pat. Off. . |
| 0294964 | 12/1987 | Japan . |
| 85-04903 | 11/1985 | PCT Int'l Appl. . |
| 8703373 | 6/1987 | PCT Int'l Appl. . |
| 8703374 | 6/1987 | PCT Int'l Appl. . |
| 8703375 | 6/1987 | PCT Int'l Appl. . |
| 8706005 | 8/1987 | PCT Int'l Appl. . |

OTHER PUBLICATIONS

Lambden et al., *Journal of Immunological Methods*, vol. 20, pp. 277-286 (1978).
Nandapalan et al., *Journal of Medical Virology*, vol. 14, pp. 285-294 (1984).
U.S. Ser. No. 155,670 (filed 2/12/88) by McClune et al.
U.S. Ser. No. 155,441 (filed 2/12/88 by Warren, III et al.).
Frankel et al., *Mol. Immunology*, 16, pp. 101-106 (1979).
Morrison-Oncology & Biotechnology News, Apr. 1988.

*Primary Examiner*—Sam Rosen
*Attorney, Agent, or Firm*—J. Lanny Tucker

[57] ABSTRACT

Diluent and wash compositions are useful in a rapid and sensitive assay for detecting antibodies, and especially retroviral antibodies, in a biological specimen. The diluent composition is buffered to a pH of 6 to 10 and includes a protein or carbohydrate, a surfactant and a negatively-charged organic compound. The wash composition is buffered to a pH of 5 to 10 and includes a surfactant. These compositions can be included in a diagnostic kit. The method of this invention includes mixing the biological specimen with the diluent composition, forming an immunological complex between ligand and antibodies in the specimen and separating complexed materials from uncomplexed materials using a filtration membrane and a washing step. An enzyme labeled anti-antibody is added to form a ligand-antibody-antibody complex followed by its detection using suitable reagents.

13 Claims, No Drawings

DIAGNOSTIC KIT AND METHOD FOR RAPID DETECTION OF ANTIBODIES

FIELD OF THE INVENTION

The present invention relates to diluent and wash compositions useful in detecting antibodies, and especially viral antibodies, in biological specimens. It also relates to a diagnostic kit containing same and to a rapid and sensitive method for the detection of those antibodies. The invention is particularly useful for the detection of retroviral antibodies.

BACKGROUND OF THE INVENTION

The immune systems of humans and animals are amazingly complex and have mechanisms for protecting the host from ill effects caused by foreign chemical or biological substances which enter the host in some manner. Such foreign substances include haptens, antigens, viruses, microorganisms, drugs, hormones, plant lectins and other substances readily apparent to one skilled in the art. In this application, such substances are identified as "ligands". When a host is invaded by a ligand, the host normally produces proteins in response which will complex specifically with the ligand. Such proteins are known as antibodies. It is often desirable to detect the presence of ligands for appropriate diagnosis and treatment.

However, sometimes, the ligand cannot be readily detected, for example where it is masked by other materials in the host or is present in very low concentrations undetectable by standard assays. Because antibodies react specifically with a corresponding ligand to form immunological complexes, the presence of antibodies is often detectable when the presence of the ligand is not. Using immunological reactions, then, it is sometimes possible to design assays to detect the antibodies as an indication of the presence of the ligand.

In other instances, antibodies are present in a host organism because of autoimmune responses, that is, in an abnormal situation when antibodies are produced against the host's normal tissues, cells or organs. Detection of the antibodies in such instances may help identify pathological activities in the host.

Viruses present in humans and animals are a major healt concern today, not only because of the effect they have upon the host organism, but also because of a continuing need for improved means for detection, diagnosis, treatment and contamination prevention. Some viruses do not harm the host organism while others merely cause minor discomfort or temporary inconveniences. Still others, however, may cause serious illness and result in death.

There are, then, obvious reasons to detect the presence of viruses in host organisms quickly for effective treatment, appropriate health safety measures or for screening biological fluids, tissues or organs which may be used by another human or animal.

Virus particles and virally infected cells contain specific antigenic components which can induce an immunological response to produce antibodies specific to the components. In some instances, the antigenic components can be detected in vitro using antibodies specific thereto. However, in other instances, it is easier or more expedient to detect the antibodies produced in the organism.

Human retroviruses, as a family, represent a group of related exogenous retroviruses which exert a significant proliferative or cytopathic effect upon the target T-lymphocytes they infect. The resulting effects of these retroviruses include T-cell proliferation leukemia, T-cell depletion and immunosuppression in humans infected by the viruses. These retroviruses are known as the HTLV (human T-cell leukemia-lymphoma virus) and HIV (human immunodeficiency virus) families of T4 tropic retroviruses.

The first human retrovirus discovered, (HTLV-I), appears to represent the etiological agent of mature T-cell leukemia and lymphomas as typified by adult T-cell leukemia (see, for example, Poiesz et al, *Proc. Nat. Acad. Sci., U.S.A.*, 77, 1980 and Yoshida et al, supra, 79, 1982). At present, the presence of HTLV-I and T-cell malignancies are believed to occur at increased rates in the populations of certain Caribbean islands and southern Japan, but HTLV-I is now widely recognized as a worldwide medical concern. People infected with HTLV-I or having come into contact with the virus generally have antibodies directed against HTLV-I in their body fluids, and especially in their blood. In addition, a significant portion of the patients suffering from the neurological disorder known as Tropical Spastic Paraparesis possess antibodies to HTLV-I.

Continuing research has determine that there are several additional retroviruses which are of significant medical importance. Besides HTLV-II, a third virus was discovered and identified variously as HTLV-III, Lymphadenopathy Associated Virus (LAV) and HIV-I (described below).

Acquired immune deficiency syndrome (AIDS) is a relatively recently recognized disease evident in several parts of the world. It has been observed that the disease is predominant in certain high-risk segments of the population of certain countries, including practicing homosexual men, illegal intravenous drug users, hemophiliacs, blood transfusion recipients and those having intimate heterosexual relationships with these high risk groups. It has been discovered by U.S. and French researchers that the disease is spread by the transmission of the retrovirus HIV-I.

No cure has been found to date for AIDS, and medical and scientific observations indicate that it is unlikely a cure will be found within the near future. Moreover, it is well known that all sufferers from the disease are likely to die. These tragic consequences have spurred the urgency in medical and diagnostic research associated with this disease.

As with other viral diseases, exposure to or infection from HIV-I produces an immunological response, that is the production of antibodies. More specifically, antibodies to antigens of the virus have been detected by researchers and clinicians in many sero-epidemiologic studies. A number of human biological fluids are considered vectors for HIV-I infection. Human blood is the primary biological fluid in which the virus or antibodies therefor are found. While people having HIV-I antibodies in their blood may not necessarily also carry the virus or themselves develop AIDS, there remains a serious concern about viral transmission through contact with or donation of blood by such individuals. Hence, there is continuing research and development to provide rapid and sensitive assays for detecting the presence of HIV-I antibodies in blood samples. Blood banks have an obvious interest in screening donated blood to insure a virus-free supply. Medical and dental practitioners in hospitals and offices need diagnostics tests to adequately protect other patients as well as themselves from viral infection.

Many immunological techniques are known for detection of antigens or antibodies, including HIV-I antibodies. For example, U.S. Pat. Nos. 4,520,113 (issued May 28, 1985 to Gallo et al) and 4,708,818 (issued Nov. 24, 1987 to Montagnier et al) describe radioimmunoassays, Western blot techniques and ELISA (enzyme-linked immunosorbent assay) for HIV-I antibody detection. A competitive ELISA is described in E.P. Publication 234,941 (published Sept. 2, 1987).

While a number of useful assays are known, they generally require hours to perform (see for example, E.P. Publication 234,941, Example 5) and may also require extensive equipment and complicated protocols in order to obtain accurate results. This adds to the expense of the test as well as the likelihood of error.

Moreover, such tedious and time-consuming tests are not suitable for instances where a determination of the presence of a retrovirus (or any other virus) is needed quickly. For example, practitioners or clinicians in police stations, trauma centers, hospital emergency rooms, immigration offices and dental and medical offices may need to know if patients are infected with a given virus immediately. A rapid viral test would be a significant advance for such instances. Also, rapid viral tests would be highly valuable for use in remote parts of the world where conventional medical or testing facilities are nonexistant.

Hence, there is a need in the art for a rapid and sensitive assay for viral antibody detection in biological specimens.

SUMMARY OF THE INVENTION

The problems of known assays are overcome with a method for the determination of antibodies comprising the steps of:

A. mixing a biological specimen suspected of containing antibodies to a specific ligand with a diluent composition buffered to a pH of from about 6 to about 10 and comprising a protein or carbohydrate, a surfactant and a negatively-charged organic compound, B. contacting the diluted specimen with the ligand to form an immunological complex of the ligand and any antibodies specific to the ligand present in the specimen, C. prior to, simultaneously with or subsequent to complex formation, insolubilizing the ligand by attachment to a solid substrate, D. simultaneously with or subsequent to the insolubilization of step C, separating the complex from uncomplexed materials using a microporous filtration membrane which retains the complex thereon, E. prior to, simultaneously with or subsequent to the separating step, contacting the complex with enzyme-labeled antibodies directed to the antibodies specific to the ligand to form a ligand-antibody-antibody-enzyme complex, F. washing the ligand-antibody-antibody-enzyme complex retained by the membrane with an aqueous wash solution to separate uncomplexed materials from the complex, and G. adding a reagent composition capable of providing a detectable species in the presence of the enzyme, and determining the presence of the species as an indication of the presence of antibodies specific to the ligand in the specimen.

The assay of this invention is rapid. That is, it generally takes less than 20 minutes to carry out. A skilled clinician can carry it out in less than 10 minutes. Moreover, the assay is sensitive, exhibits very low background (that is, very few false positives) and is relatively inexpensive compared to the complicated and time-consuming assays known in the art. The present invention is useful to a great advantage to detect antibodies produced in response to any biological condition or ligand (and particularly in response to retroviral antibodies) in situations where rapid testing is needed or where more complicated tests are unavailable or hard to use. For instance, the present invention can be packaged as a diagnostic kit for use in medical and dental offices, hospitals, trauma centers, police stations, immigration offices or remote areas of the world.

The advantages of the present invention are achieved because of the use of certain diluent and wash compositions. The diluent composition is buffered at a pH of from about 6 to about 10 and comprises a protein or carbohydrate, a surfactant and a negatively-charged organic compound. The aqueous wash composition is buffered at a pH of from about 5 to about 10, and comprises a surfactant. In one embodiment, the wash composition also comprises a water-miscible polar organic solvent and an alkali metal or ammonium salt present in an amount to provide an ionic strength of at least about 0.25. The diluent and wash compositions can be packaged as a diagnostic kit.

DETAILED DESCRIPTION OF THE INVENTION

The kit and assay of the present invention can be used to rapidly detect the presence of antibodies in a biological specimen from human or animal hosts. Biological samples which can be so assayed include, but are not limited to, whole blood or a component (serum or plasma) thereof, saliva, lacrimal fluid, spinal fluid, feces, urine, vaginal secretions, seminal fluid, human tissue or organ extracts and human milk. This invention is particularly useful for assaying human serum or plasma.

Antibodies to any chemical or biological ligand can be detected with this invention. This ligand can be a foreign substance (antigen, virus, hapten, drug, hormone, plant lectin, toxin, microorganism and others readily apparent in the art) which invades the host. Alternatively, the antibodies can be produced from autoimmune responses in the host.

This invention is particularly useful to detect antibodies to human or animal viruses including, but not limited to, antibodies to retroviruses (described in detail above), influenzas, herpes, hepatitis, cytomegalavirus, Epstein barr virus and rubella. In particular, antibodies to any of HTLV-I and -II, HIV-I and -II, individually or together, can be detected, with antibodies to HIV-I being of greatest interest.

Because a biological specimen (such as serum or plasma) obtained from a patient may contain a ligand (such as a virus, which would present a health hazard to those carrying out the assay) as well as its antibodies, it may be desirable to treat the specimen in a suitable manner to inactivate the ligand without affecting the antibodies to be detected. For example, useful viral inactivation techniques include heat treatment for suitable times at suitable temperatures, sonication or treatment with surfactants, alcohols, peroxides, dextran sulfate, bleach or other reagents which kill the virus. Other techniques would be readily apparent to one skilled in the art. The virus can be inactivated before use in the assay, or during the early steps of the assay of this invention.

Detection of antibodies to a specific ligand is accomplished by firstly mixing the specimen with the aqueous diluent composition of this invention. This composition includes one or more proteins or carbohydrates which are in their unmodified or underivatized state, as opposed to the proteins and carbohydrates described below which are modified in some manner to put additional negative charges thereon. These proteins or carbohydrates can be used individually or in mixtures. Representative materials include, but are not limited to, gum arabic, dextran, gelatin, argot, and human or animal serum or components thereof (for example, bovine serum albumin, fetal calf serum, rabbit serum, human serum or goat serum). Gum arabic and bovine serum albumin are preferred. This protein or carbohydrate is generally present in an amount of at least about 0.5, and preferably from about 0.5 to about 10 weight percent (based on total composition weight).

The specimen and diluent composition are mixed in a suitable vessel generally at a temperature of from about 10° to about 40° C., and preferably at from about 15° to about 25° C. The mixing time is generally a few seconds but longer times can be used if desired.

The composition also includes one or more buffers which maintain the pH of the composition at from about 6 to about 10, and preferably at from about 7.5 to about 8.5. Useful buffers are well known in the art and include, but are not limited to, tris(hydroxymethyl)aminomethane, phosphate, glycine, morpholinopropanesulfonic acid, morpholinoethanesulfonic acid and others known in the art.

Further, the diluent composition contains one or more water-soluble or water-dispersible surfactants. These surfactants can be nonionic, anionic or amphoteric. Any suitable surfactant can be used that does not adversely affect the complexation of viral antigen and corresponding antibodies or the ability of the other components in the diluent composition to provide desired sensitivity.

Particularly useful surfactants include nonionic surfactants including, but not limited to, polyoxyethylene derivatives, for example ethoxylated fatty esters or mixtures thereof. Representative examples include polyoxyethylene sorbitan monolaurate, polyoxyethylene sorbitan monopalmitate, polyoxyethylene sorbitan monostearate. Representative ethoxylated fatty esters are marketed under the Tween tradename (ICI Americas, Inc.) and T-MAZ (trademark of Mazer Chemicals). Tween-20 is a particularly useful nonionic surfactant. The surfactant is generally present in an amount of at least about 0.01, and preferably from about 0.1 to about 3, weight percent.

The diluent composition also comprises a negatively-charged organic compound, or mixture thereof. The compound provides a highly negative environment for the assay so that non-specific interactions by the antibodies and antigens are significantly reduced. This environment can be provided by chemically modified proteins or carbohydrates, anionic surfactants, negatively-charged buffers or other chemical or biological compounds having the requisite negative charges to effectively repel other negatively charged materials within the diluent and biological specimen.

Particularly useful negatively-charged compounds are water-soluble proteins or carbohydrates which have been modified in some manner to provide a compound with a low pI. These compounds generally have a pI of less than or equal to about 5. A mixture of proteins or carbohydrates having the desired pI can also be used. The term pI (or isoelectric point) is known as the pH at which there is an equal number of positive and negative charges in a molecule so that the molecule is neutral in charge. The pI can be measured using standard materials and procedures. For example, it can be measured by isoelectric focusing using an LKB Ampholine PAG plate (available from LKB-Produkter AB, Bromma, Sweden), having a pH range 3.5–9.5, and standard calibrators.

Useful modified proteins include casein derivatives or other protein derivatives which are negatively charged (for example, derivatives obtained from acylation, alkylation or sulfonation of casein, such as succinylated casein, succinylated bovine serum albumin, carboxymethyl casein, and succinylated collagen). These materials are readily prepared by acylating, alkylating or sulfonating a protein having available amine groups using suitable conditions. Useful acylating agents include, but are not limited to, those described in U.S. Pat. No. 4,591,571 (issued May 27, 1986 to Kuboyama et al), such as anhydrides, acyl halides and esters derived from dicarboxylic and polycarboxylic acids. Alkylation and sulfonation are generally described in copending U.S. Ser. No. 98,432 filed Sept. 18, 1987 by Warren III et al. The preparation of succinylated casein is described below.

Alkylating and sulfonating agents useful in modifying proteins include, but are not limited to, bromoacetic acid, chloroacetic acid, fluoronitrobenzene, m-(chlorosulfonyl)benzoic acid, bromomalonic acid, bromopropionic acid and p-(chlorosulfonyl)benzoic acid.

Useful low pI carbohydrates include water-soluble cellulose derivatives, such as carboxymethyl cellulose, carboxyethyl cellulose and others which would be readily apparent to one skilled in the art. Such materials are generally commercially available.

Preferred low pI proteins and carbohydrates include succinylated casein, carboxymethyl cellulose, succinylated bovine serum albumin and succinylated collagen. Succinylated casein is most preferred.

The low pI protein or carbohydrate is present in an amount of at least about 0.1, and preferably from about 1 to about 3, weight percent (based on total composition weight).

The diluent can also comprise one or more viral inactivation agents, such as a peroxide or dextran sulfate, which will not interfere or deleteriously affect the other components of the diluent composition.

Once the specimen has been mixed with the diluent composition, the diluted specimen is then contacted with the appropriate ligand reactive with the antibodies in the specimen. If antibodies are present, this contact produces an immunological complex of ligand and antibodies directed to the ligand. This contact and formation of complex takes place quickly, usually within 5 minutes and preferably within 1 minute. The diluted specimen and immunological reagents are generally mixed together for a suitable period of time and incubated at a temperature of from about 15° to about 30° C., and more likely at 18° to 25° C.

In one embodiment, the ligand and antibodies react to form a water-soluble complex which is further reacted to form an insoluble complex. For example, the ligand could be biotinylated for attachment to avidin on an insoluble substrate. Other attachment means are known in the art. The soluble complex could also be further reacted with other antibodies which are specific for the ligand or anti-antibodies specific for the antibodies which are specific for the ligand in the specimen.

In a preferred embodiment, the ligand is attached to an insoluble substrate so that the resulting complex is insolubilized by the complexation reaction. Suitable substrates include, but are not limited to magnetic particles, glass or polymeric particles, glass or polymeric fibers, membranes, the sides of test tubes, test devices, microtiter wells and others readily apparent to one skilled in the art. Attachment of ligand to the substrate can be accomplished in any suitable manner, for example by absorption or covalent attachment through reactive groups, avidin-biotin linkages, protein or other linking compounds or other techniques known in the art.

More preferably, the ligand is part of an immunological reagent comprising polymeric particles to which the ligand is suitably attached. The reagent can be formed from polymeric particles of any suitable composition. Many suitable particles are known in the art which are prepared from polyamides, polycarbonates, polyvinyl aromatics, polyesters or other polymers. The exact composition may be dependant upon the method of attachment of the ligand and the particular ligand density desired. Generally, the surface density of the ligand on the particles is sufficient to provide acceptable sensitivity in the assay. It will vary with the ligand being attached. If the method of ligand attachment is adsorption, the type of useful polymeric particles may be composed of certain materials whereas other materials are more useful for covalent attachment, which is preferred. Methods of attachment, such as those noted above, are well known in the art. Covalent attachment of ligand is usually accomplished using surface reactive groups which are capable of reacting directly with free amine or sulfhydryl groups of the ligand or through linkages (for example avidin-biotin or proteins). Such surface reactive groups include, but are not limited to, carboxy, epoxy, aldehyde, active halo atoms, activated 2-substituted ethylsulfonyl and other groups known in the art. The following discussion regarding preferred embodiments is for exemplification only, and is not meant to be limiting.

Particularly useful polymeric particles are those described and claimed in copending U.S. Ser. No. 136,165, filed Dec. 18, 1987 by Sutton et al. Such particles are generally water-insoluble latex particles having an average particle size greater than about 0.01 micrometers. They are composed of polymers prepared from one or more ethylenically unsaturated polymerizable monomers at least one of which has active halo atoms or activated 2-substituted ethylsulfonyl or vinylsulfonyl groups.

Monomers having an active halogen atom include vinyl chloroacetate, vinyl bromoacetate, haloalkylated vinyl aromatics (for example, chloromethylstyrene or bromomethylstyrene), haloalkyl acrylic or methacrylic esters (for example, chloroethyl methacrylate, 3-chloro-2-hydroxypropyl methacrylate and 3-chloropropyl acrylate) and others known to one skilled in the art. The haloalkylated vinyl aromatics, for example those having active haloalkyl groups of 1 to 3 carbon atoms, are preferred when the active halogen atom is used as the reactive group. Chloromethylstyrene is most preferred.

Preferred activated 2-substituted ethylsulfonyl and vinylsulfonyl monomers can be represented by the formula (I):

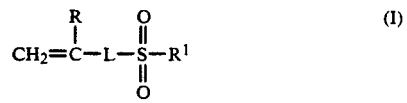

wherein R is hydrogen or substituted or unsubstituted alkyl (generally of 1 to 6 carbon atoms, such as methyl, ethyl, isopropyl or hexyl. Preferably, R is hydrogen or methyl.

$R^1$ is $-CH=CHR^2$ or $-CH_2CH_2X$ wherein X is a leaving group which is displaced by a nucleophile or is eliminated in the form of HX by treatment with a base (such as halo, acetoxy, alkylsulfonyloxy such as methylsulfonyloxy, arylsulfonyloxy such as p-tolylsulfonyloxy, trialkylammonio, for example, a trimethylammonio salt or pyridinio salt). $R^2$ is hydrogen, substituted or unsubstituted alkyl (generally of 1 to 6 carbon atoms as defined for R), or substituted or unsubstituted aryl (generally of 6 to 12 nuclear carbon atoms, such as phenyl, naphthyl, xylyl or tolyl). Preferably, $R^1$ is $-CH_2CH_2X$. This group, which is an activated 2-substituted ethyl group, can be substituted with any group which does not impair the displacement of the leaving group X.

L is a linking group which can be a substituted or unsubstituted alkylene generally having 1 to 20 carbon and hetero atoms in the backbone. This definition of alkylene is meant to include alkylene groups interrupted or terminated with oxy, thio, $-NR^3-$ [wherein $R^3$ is hydrogen, substituted or unsubstituted alkyl of 1 to 6 carbon atoms (such as methyl, chloromethyl or 2-hydroxyethyl) or substituted or unsubstituted aryl of 6 to 10 carbon atoms (such as phenyl, naphthyl or xylyl)], ester (—COO—), amide (—CONH—), urylene

sulfonyl (—SO$_2$—), carbonate, sulfonamide, azo, phosphono or other similar groups. Representative alkylene groups include methylene, ethylene, isobutylene, hexamethylene, carbonyloxyethyleneoxycarbonylethylene, methylenebis(iminocarbonyl)ethylene, carbonyloxydodecylenecarbonyloxyethylene, carbonyliminomethyleneiminocarbonyliminoethylene, carbonyliminomethyleneiminocarbonylethylene and other groups described or suggested by U.S. Pat. Nos. 4,161,407 and 4,548,870, noted above.

L can also be substituted or unsubstituted arylene generally having 6 to 12 nuclear carbon atoms. Representative arylene groups include phenylene, tolylene, naphthylene and others noted in the patents mentioned above. Also included in this definition of L are divalent groups which are combinations of one or more of each of the alkylene and arylene groups defined above (for example, arylenealkylene, alkylenearylenealkylene and others readily determined by one of ordinary skill in the art), as well as such combinations which are interrupted or terminated by one or more amide or ester groups (for example, carbonyliminoarylenealkylene). Preferably, L is substituted or unsubstituted phenylenealkylene [for example, substituted with one or more alkyl groups (as defined for R), alkoxy groups (generally of 1 to 6 carbon atoms, for example, methoxy, propoxy or butoxy) or halo groups], carbonyliminoarylenealkylene (wherein arylene and alkylene are defined above), or carbonyliminoalkyleneiminocarbonylalkylene (wherein alkylene are defined above).

Representative useful monomers include m & p-(2-chloroethylsulfonylmethyl)styrene, m & p-[2-(p-tolylsulfonyloxy)ethylsulfonylmethyl]styrene, m & p-vinylsulfonylmethylstyrene, N-[m & p-(2-chloroethylsulfonylmethyl)phenyl]acrylamide, and N-[2-(2-chloroethylsulfonyl)ethylformamidomethyl]acrylamide. The first monomer is preferred.

One or more of the monomers described above can be polymerized individually or in combination to form homo- or copolymers. Alternatively, and preferably, one or more of them are copolymerized with at least one other ethylenically unsaturated polymerizable monomer. Generally such monomers provide various desirable properties such as hydrophobicity, dispersibility or other features. Particularly useful comonomers are described in copending U.S. Ser. No. 136,165 (noted above).

Representative useful polymers include the following: poly(m & p-chloromethylstyrene), poly(styrene-co-m & p-chloromethylstyrene-co-2-hydroxyethyl acrylate) (67:30:3 molar ratio), poly(styrene-co-m & p-chloroethylsulfonylmethylstyrene) (95.5:4.5 molar ratio), poly{styrene-co-N-[m & p-(2-chloroethylsulfonylmethyl)phenyl]acrylamide} (99.3:0.7 molar ratio), poly(m & p-chloromethylstyrene-co-methacrylic acid)(95:5, 98:2 and 99.8:0.2 molar ratio), poly(styrene-co-m & p-chloroethylsulfonylmethylstyrene-co-methacrylic acid)(93.5:4.5:2 molar ratio), poly{styrene-co-N-[m & p-(2-chloroethylsulfonylmethyl)phenyl]acrylamide-co-methacrylic acid}(97.3:0.7:2 molar ratio), and poly(styrene-co-m & p-chloromethylstyrene)(70:30 molar ratio).

In preparing an immunological reagent, ligand (such as viral antigen) is generally mixed with the particles under suitable conditions depending upon the method of attachment (absorption or covalent). For attachment to the preferred particles described above having reactive halo atoms, activated 2-substituted ethylsulfonyl or vinylsulfonyl groups, the ligand is generally mixed with the particles for up to 24 hours at a temperature of from about 20° to about 40° C. The particle suspension is generally buffered to a pH of from about 7 to about 10. In the mixture, particles are generally present in an amount of at least about 0.2 weight percent, and ligand is generally present in an amount of at least about 1% (based on total weight of particles).

Viral antigen useful in the practice of preferred embodiments can be prepared in any suitable manner. For example, it can be isolated from biological sources such as cell cultures or infected animal or human hosts, or synthesized using various biotechnological techniques.

In preferred embodiments, retroviral antigen can be obtained in any suitable manner. It can be naturally occurring viral substances or components thereof, or synthetic peptides, or polypeptides produced using recombinant DNA technology as described, for example, in PCT Publications 86/01834 (University of California, Berkeley) and 86/02930 (Harvard University) and U.S. Pat. No. 4,725,669 (issued Feb. 16, 1988 to Essex et al). Other technical and patent references describing synthetic methods for producing HTLV-I, HTLV-II, HIV-I, HIV-II and other retroviral antigen are too numerous to mention here.

For example, a preferred manner of obtaining HIV-I antigen is to culture the virus in a suitable cell line followed by removal of the virus from the cell. The removed virus, or component thereof, is immobilized as described above on the polymeric particles to form a reagent. For example, HIV-I viral antigen can be obtained by detergent lysis of HIV-I viral particles isolated from a suitable host cell line. Such cell lines, which are permissive to the growth of HIV-I, include but are not limited to: Hut 78 (ATCC TIB 161), H9 (ATCC No. CRL 8543), Molt 3, CEM, OKT4+, Ti7.4, HT and clones thereof, and others as described, for example, in U.S. Pat. Nos. 5,647,773 (issued Mar. 3, 1987 to Gallo et al) and 4,652,599 (issued Mar. 24, 1987 to Gallo et al). Viral particles can also be isolated from new cell lines established from patients having AIDS or what is known as "pre-AIDS" (chronic generalized lymphadenopathy which often precedes AIDS). In addition, antigenic material can be obtained from HIV-infected persons. Cultivation of the cells and isolation of viral particles are carried out using known methods. The viral particles can be obtained from multiplied cells as well as the supernatant by lysis with a detergent or surfactant. The Hut 78 cell line, once infected with HIV-I, is preferred in obtaining HIV-I antigens.

A preferred method for obtaining HTLV-I antigen is by lysing HTLV-I viral particles isolated from a suitable host cell line. Such cell lines include, but are not limited to Hut 102 and MT-2 and clones thereof. The Hut 102 cell line, which is available from the American Type Culture Collection (ATCC TIB 162), is preferred. HTLV-I can also be isolated from new cell lines established from peripheral blood T-cells or tissues obtained from cutaneous T-cell leukemia/lymphoma patients. Cultivation of the cells and isolation of antigen are carried out using known procedures. HTLV-II antigens can be similarly obtained.

Once the immunological complex has been formed and insolubilized in some manner, it is separated from the uncomplexed materials using a microporous filtration membrane which has pores large enough to allow uncomplexed materials to pass through while retaining the complex. Complex insolubilization can occur substantially simultaneously with separation, or prior thereto. Such membranes can be constructed of any suitable water-insoluble material which will maintain its integrity during the assay. Such materials include, but are not limited to, filter papers, porous particulate structures, porous polymeric films, cellulose, glass fibers, woven and nonwoven fabrics, polymeric filters and others known in the art. Particularly useful membranes are the polyamides (for example nylon) marketed by Pall Corp., for example, the membrane marketed under the trademark LOPRODYNE. The membrane useful in this invention can be further treated or coated if desired (for example with surfactants, polymers or proteins) to enhance separation or fluid flow or to reduce nonspecific interactions.

The membrane can be used as a separate substrate with suitable containers for carrying out the assay of this invention. Preferably, however, it is mounted as part of a test device. Various test devices are known in the art including those described in U.S. Pat. Nos. 3,825,410 (issued July 23, 1974 to Bagshawe), 3,888,629 (issued June 10, 1975 to Bagshawe), 3,970,429 (issued July 20, 1976 to Updike) and 4,446,232 (issued May 1, 1984 to Liotta). Particularly useful devices are described in copending U.S. Ser. No. 98,248 (filed Sept.

18, 1987 by Hinckley et al) now U.S. Pat. No. 4,921,677 and in copending U.S. Ser. No. 136,211 (filed Dec. 18, 1987 by Smith-Lewis) now U.S. Pat. No. 4,870,007.

More specifically, the test device comprises a water-insoluble substrate having one or more test zones therein each of which can accommodate a sample of a biological specimen and appropriate reagents.

The substrate can be prepared from any useful water-insoluble material such as glass, polymeric materials, fibrous materials, cellulosic materials and other materials known in the art.

In a preferred embodiment, the test device has three test zones or wells designed for providing a test result and positive and negative control results. Each test well has a microporous membrane mounted therein. Another test device is described and claimed in copending and commonly assigned U.S. Ser. No. 19,810 (filed Feb. 27, 1987 by Hinckley). Other variations of useful test devices would be within the purview of a worker of ordinary skill in the art. The immunological reagent described above can be incorporated into the disposable test device, if desired, for example as a coating on the membrane. Alternatively, the reagent can be separately added during the assay.

Separation of the immunological complex from uncomplexed materials occurs virtually simultaneously with contacting the membrane with the specimen. In other words, it takes only a few seconds, and at most a minute or two for the specimen to drain through the membrane while the immunological complex is retained thereon.

The immunological complex formed between the ligand and any antibodies in the specimen is contacted with an enzyme-labeled conjugate of antibodies directed to the ligand antibodies to form a complex of labeled antibody-antibody-ligand. This contact can occur prior to, simultaneously with or subsequent to the separation step described above. In addition, this complex can be water-soluble. That is, it is formed prior to insolubilizing the ligand. In preferred embodiments, however, the ligand is insolubilized prior to forming the ligand-antibody-antibody complex. Also, in preferred embodiments, separation of uncomplexed materials from the ligand-antibody complex occurs prior to forming the ligand-antibody-antibody complex. The insoluble complex is collected on the filtration membrane for subsequent detection.

Conjugates of enzymes and anti-antibodies are prepared using standard starting materials and well known preparatory procedures. Some conjugates are commercially available. Useful enzyme labels include, but are not limited to, peroxidase, glucose oxidase, alkaline phosphatase, urease and $\beta$-galactosidase. Peroxidase (in any of its forms and from any source) is preferred. The antibodies can be monoclonal or polyclonal, or whole antibodies or parts of antibodies as long as they react with the antibodies to the ligand in the assay. For example, they can be goat or mouse anti-human antibodies. The conjugate can be used in admixture with other materials including buffers, surfactants, proteins and peroxidase rate enhancers. A particular conjugate composition is described in detail below.

Forming the ligand-antibody-antibody complex generally occurs upon incubating the materials for up to 5 minutes at a temperature between about 15° C. to about 30° C. Preferably, the incubation is carried out at from about 15° C. to about 25° C. for about one minute. When the complex is insolubilized, any fluid from the conjugate composition is drained through the filtration membrane immediately.

The insoluble complex thereby formed is washed to remove uncomplexed materials with an aqueous wash composition which is buffered at a pH of from about 5 to about 10 use or more suitable buffers, and comprises a surfactant. Generally, only a few drops of wash composition are needed to remove the uncomplexed materials through the filtration membrane. Preferably, the pH of the wash composition is from about 6.5 to about 8.5.

In one embodiment, the wash composition comprises at least about 0.01 weight percent of a surfactant comprising a dodecyl sulfate anion and an alkali metal or ammonium cation, as described, for example in copending U.S. Ser. No. 155,670, filed Feb. 12, 1988 by McClune et al. In another embodiment, the wash composition comprises at least about 1.5 weight percent of a surfactant comprising a lower alcohol sulfate anion having from 6 to 10 carbon atoms and an alkali metal or ammonium cation, as described for example, in copending U.S. Ser. No. 155,441, filed Feb. 12, 1988 by Warren III et al now U.S. Pat. No. 4,965,191. Particularly useful wash compositions are described below.

In still another embodiment, a novel wash composition includes a water-miscible polar organic solvent which generally has a molecular weight less than about 200. Useful solvents include amides (for example 1-methyl-2-pyrrolidinone, N,N-dimethylformamide and N,N-dimethylacetamide), ketones (for example acetone, methyl ethyl ketone and 3-pentanone), alcohols (for example methanol, ethanol, t-butanol and isopropanol). Tert-butanol and 1-methyl-2-pyrrolidone are preferred.

Useful surfactants in this wash composition are nonionic, anionic or amphoteric surfactants. Useful nonionic surfactants include the polyoxyethylene derivatives described above, octylphenoxy polyethoxyethanol surfactants, fluorocarbon surfactants and others readily apparent to one skilled in the art. Anionic surfactants include, for example, deoxycholic acid and derivatives thereof, alkyl sulfate esters and others readily apparent to one skilled in the art.

One or more simple water-soluble salts are also present in the novel wash composition, including alkali metal and ammonium salts, such as lithium chloride, sodium chloride, potassium chloride, sodium iodide, ammonium chloride, ammonium sulfate and others known in the art. The salts are present in amount sufficient to provide an ionic strength of at least about 0.25, and preferably from about 0.25 to about 1. A representative wash composition is described below.

The insoluble complex retained on the membrane is contacted with a reagent composition which comprises one or more reagents for providing a detectable species upon reaction with the enzyme label. The reagents will then depend upon the enzyme, and for each enzyme there are many known reagents for this purpose. One or more reactions may be necessary to form the detectable species.

In a preferred embodiment where the enzyme is peroxidase, the reagent composition comprises suitable reagents for forming a detectable species (chromogen or fluorogen) in the presence of hydrogen peroxide and peroxidase. This reagent composition includes appropriate reagents, one of which acts as a substrate for peroxidase, which are capable of providing a detectable dye in the presence of peroxidase and hydrogen peroxide. The substrate itself can be a dye-forming compound, such as benzidine, tetramethylbenzidine or other benzidine derivatives, 2,2'-azino-di-(3-ethyl-benzthiazolone-6-sulfonic acid), phenol red, o-phenylenediamine, pyrogallol, 4-aminoantipyrine, bromopyrogallol red and others known in the art. Alternatively, a hydrogen donor and an electron acceptor can be combined to provide a detectable species (for example, see the compounds described in U.S. Pat. No. 4,260,679).

Preferably, the reagent composition includes a leuco dye which provides a dye in the presence of hydrogen peroxide and peroxidase [for example, a triarylimidazole leuco dye as described in U.S. Pat. Nos. 4,089,747 (issued May 16, 1978 to Bruschi) or a triarylmethane leuco dye as described in 4,670,385 (issued June 2, 1987 to Babb et al)]. A preferred dye-providing composition is described and claimed in copending U.S. Ser. No. 136,166, filed Dec. 18, 1987 by McClune.

Once a dye has formed in the presence of the insoluble complex, it can be evaluated visually or using spectrophotometric equipment to determine if the assay indicates the presence of ligand antibodies in the specimen. Both positive and negative control tests may be desirably carried out with the specimen test. Appropriate reagents would be used for each control test to give the desired result.

The kit of this invention can include the diluent and wash compositions described herein which are packaged in a suitable manner and included in a carrier of some type which can be compartmentalized to receive one or more containers holding the compositions. In addition, it can also include one or more of the following which are useful in carrying out the method: disposable test device containing a filtration membrane, reagent composition, enzyme-labeled antibody composition, and an immunological reagent. Reagents can be provided in dry form or in appropriate solutions. Non-reactive components of the kit can include instructions, mixing vessels, stirring means, pipettes and the like.

The following compositions were used in carrying out the assay described in the illustrated example below. All percentages are by total weight of the composition.

Immunological Reagent

This reagent comprised particles of poly[styrene-co-m & p-(2-chloroethylsulfonylmethyl)styrene] (95.5:4.5 molar ratio) onto which were covalently attached HIV-I antigen.

HIV-I antigen was prepared by culturing HIV-I in the Hut 78 cell line in Roswell Park Memorial Institute-1640 medium in the presence of 10% bovine serum albumin and gentamycin (50 $\mu$g/ml). The cell density was maintained at approximately $10^5$–$10^6$ cells/ml, and the cells were subcultured by the addition of fresh medium to maintain this density. The viral particles were isolated in a closed-system stainless steel filtration/concentration apparatus by pooling the cultures to be harvested in a holding tank which permits the cell culture fluid to be pumped through a filter housing fitted with a 0.45 $\mu$m filter. This first filtration step removed whole cells and cell debris. The cell-free supernatant was then pumped through a second filter housing fitted with a 0.2 $\mu$m filter in order to eliminate any residual cell debris not removed by the 0.45 $\mu$m filter. The second supernatant was pumped through a concentration cassette fitted with a 100,000 dalton cutoff membrane to concentrate the preparation to a suitable volume. The crude viral particles thus obtained were pelletized by centrifugation for two hours at about 50,000×g and resuspended in about 40 ml of a buffer solution [pH 7.8, 0.01 molar tris(hydroxymethyl)aminomethane hydrochloride, 0.01 molar NaCl, 0.001 molar ethylenediaminetetraacetic acid] layered over a 1300 ml linear 22–65% sucrose gradient in the buffer with a conventional zonal rotor and ultracentrifuged overnight at about 30,000×g. The gradient was fractionated into about 110 fractions (12 ml each) and all fractions with densities between 1.14 and 1.18 g/ml were pooled, diluted 3- to 4-fold with the buffer and centrifuged at about 50,000×g for two hours to recover the purified HIV-I viral particles. The particles were then suspended in 10 ml of a solution containing 0.6 molar KCl and 0.5% of a nonionic octylphenoxy polyethoxyethanol surfactant, sonicated with three 5-second bursts, incubated for one hour at 37° C. and centrifuged at 80,000×g for one hour to remove debris. The solubilized HIV-I preparation was then extracted twice with an equal volume of anhydrous ether and the resulting aqueous phase was used as the the source of HIV-I antigen in the following example.

Diluent Compositions

Two diluent compositions of this invention were prepared:

(1) succinylated casein (1%), gum arabic (1%), Tween 20 nonionic surfactant (0.05%) and Thimerosal (0.01%) in 0.1 molar Tris buffer (pH 8), and (2) succinylated casein (1%), bovine serum albumin (4%), Tween 20 nonionic surfactant (0.05%) in 0.1 molar Tris buffer (pH 8).

Wash Compositions

Two wash compositions of this invention were also prepared:

(1) 1-methyl-2-pyrrolidinone (10%), Tween 20 nonionic surfactant (0.25%), Nonidet P-40 nonionic surfactant (0.1%), sodium chloride (0.5 molar) in 0.05 molar sodium phosphate buffer (pH 7.4), and (2) sodium decyl sulfate (2.4%) in 0.1 molar sodium phosphate buffer (pH 7.2).

Two peroxidase-antibody compositions were prepared:

(1) horseradish peroxidase conjugated to rabbit anti-human antibodies, diluted 1:3000, 4% bovine serum albumin and Thimerosal preservative (0.01%) in 0.5 molar phosphate buffered saline, and (2) the same conjugate with succinylated casein (1%), 4'-hydroxyacetanilide (0.15%), bovine serum albumin (1%) in 0.1 molar Tris buffer (pH 8).

Dye-Providing Reagent Composition

A composition for providing a dye in the presence of hydrogen peroxide and peroxidase was prepared as follows: a leuco dye solution was prepared by dissolving 2-(4-hydroxy-3,5-dimethoxyphenyl)-4,5-bis(4-methoxyphenyl)imidazole (to make a 0.1% solution) in a solution of 20% poly(vinyl pyrrolidone) in sodium phosphate buffer (5 mmolar). This solution was then added to a solution containing hydrogen peroxide (10 mmolar), 4'-hydroxyacetanilide electron transfer agent (5 mmolar) and diethylenetriaminepentaacetic acid chelating agent (10 $\mu$molar) in sodium phosphate buffer to produce a final concentration of 1% poly(vinyl pyrrolidone) and 0.005% leuco dye.

Preparation of Succinylated Casein

Succinylated casein was prepared by reacting casein with an equal weight of succinic anhydride for four hours at 25° C. in 0.5 molar phosphate buffer (pH 8.5), then purifying the product by dialysis.

EXAMPLE 1

Assay of Blood Serum Specimen for HIV-I Antibodies

A human serum specimen was assayed for the presence of antibodies to HIV-I in the following manner and using a disposable test device like that described in U.S. Ser. No. 98,248 (noted above).

This test device had three test wells, each with a LOPRODYNE filtration membrane commercially available from Pall Corp. The membrane had been coated with FC 134 surfactant (0.05 g/m$^2$, available from DuPont). A positive control test well contained: a sample (0.23 mg) of the immunological reagent described above and heat treated serum containing inactivated HIV-I. A negative control test well contained the polymeric particles as used in the test well, but the particles were coated with casein only. The test well designed for receiving the test specimen contained only the immunological reagent described above.

A human serum speciment (50 μl) was mixed with a sample (5 ml) of the first diluent composition described above for a 100:1 dilution. The diluted specimen (100 μl) was then added to each of the test wells and incubated at room temperature for about two minutes to allow formation of an insoluble immunological complex, followed by fluid drainage.

The peroxidase labeled-anti-antibody composition (40 μl) was added and the insoluble labeled antibody-antibody-antigen complex was allowed to form without fluid drainage during a one minute incubation period at room temperature. Upon draining the liquid, this resulting complex was washed twice with the first wash composition described above (first with 240 μl, then with 60 μl) to separate uncomplexed materials from the complex.

A sample (40 μl) of the dye-providing composition described above was added. After two minutes incubation at room temperature, a red dye was observed in the specimen test well which indicated the presence of HIV-I antibodies in the serum specimen. The negative control well showed little background, and the positive control well showed a positive test as well.

EXAMPLE 2

Assay for HIV-I Antibodies Using Different Diluent and Wash Compositions

A human serum specimen was assayed for the presence of antibodies to HIV-I using test assays which were similar to that of Example 1 except for different diluent and wash compositions, and a number of other minor changes. Disposable test devices like that described in U.S. Ser. No. 98,248 (noted above) were used. In addition, a number of comparative Control assays were performed. These assays are outside the scope of this invention.

Each test device had three test wells, each with a nylon filtration membrane commercially available from Pall Corporation. A positive control test well contained: a sample (0.15 mg) of the immunological reagent described above and heat treated serum containing inactivated HIV-I. A negative control test well contained the polymeric particles as used in the test well, but the particles were coated with casein only. The test well designed for receiving the test specimen contained only the immunological reagent described above.

A human serum specimen was mixed with a sample of the second diluent composition (containing BSA instead of gum arabic) described above for a 80:1 dilution. The diluted specimen (100 μl) was then added to each of the test wells and incubated at room temperature for about three minutes to allow formation of an insoluble antibody-antigen immunological complex, followed by fluid drainage.

The peroxidase-labeled-anti-antibody composition (50 μl) was added and an insoluble labeled-antibody-antibody-antigen complex was allowed to form without fluid drainage during a one minute incubation period at room temperature. Upon draining the liquid, the resulting complex was washed twice with the decyl sulfate wash composition described above (first with 240 μl, then with 60 μl) to separate uncomplexed materials from the complex.

A sample (40 μl) of the dye-providing composition described above was added. After one minute incubation at room temperature, a red dye was observed in the wells and visually graded by comparison to a color gradient chart (values 0-10, with 10 representing the densest color).

Test and Control compositions are shown in Table I and the results are shown in Table II.

TABLE I

| | |
|---|---|
| Test A: | diluent composition 1, wash composition 1 and peroxidase-antibody composition 1. |
| Test B: | diluent composition 2, wash composition 1 and peroxidase-antibody composition 1. |
| Test C: | diluent composition 2, wash composition 2 and peroxidase-antibody composition 2. |
| Control A: | wash composition 1, peroxidase-antibody composition 1, and diluent composition 1 without gum arabic, succinylated casein and surfactant. |
| Control B: | wash composition 1, peroxidase-antibody composition 1, and diluent composition 2 without succinylated casein and surfactant. |
| Control C: | wash composition 2, peroxidase-antibody composition 2 and diluent composition 2 without succinylated casein and surfactant. |
| Control D: | peroxidase-antibody composition 1, diluent composition 1, and wash composition 1 without surfactant and 1-methyl-2-pyrrolidinone. |
| Control E: | peroxidase-antibody composition 2, diluent composition 2, and wash composition 2 without surfactant. |

TABLE II

| | Negative Control Well | Sample Well | Positive Control Well |
|---|---|---|---|
| Test A: | 2 | 3.3 | 7 |
| Test B: | 1 | 2.7 | 6 |
| Test C: | 2.3 | 5 | 6 |
| Control A: | 4.7 | 5 | 6.3 |
| Control B: | 4 | 4.7 | 7.7 |
| Control C: | 3.3 | 4 | 7.3 |
| Control D: | 6.7 | 5.7 | 6.7 |
| Control E: | 7.7 | 7.7 | 7.7 |

The tests showed low background (negative control well) and adequate sensitivity (difference of at least one between negative control well and sample well), while the Controls showed high background and poor sensitivity.

The invention has been described in detail with particular reference to preferred embodiments thereof, but it will be understood that variations and modifications can be effected within the spirit and scope of the invention.

We claim:

1. A method for the determination of antibodies comprising the steps of:
   A. mixing a biological specimen suspected of containing antibodies specific to a ligand with a diluent composition buffered to a pH of from about 6 to about 10 and comprising:
      an unmodified or underivatized protein or carbohydrate selected from the group consisting of gum arabic, dextran, gelatin, argot, and human or animal serum or a component thereof,
   a surfactant, and
   a water-soluble, negatively-charged protein or carbohydrate,
   B. contacting said diluted specimen with said ligand to form an immunological complex of said ligand and any antibodies specific to said ligand present in said specimen,
   C. prior to, simultaneously with or subsequently to said complex formation, insolubilizing said ligand by attachment to a solid substrate,
   D. simultaneously with or subsequent to said attachment in step C, separating said complex from uncomplexed materials using microporous filtration membrane which retains said complex thereon,
   E. prior to, simultaneously with or subsequently to said separating step, contacting said complex with enzyme-labeled antibodies specific to said antibodies specific to said ligand to form a ligand-antibody-antibody-enzyme complex,
   F. washing said ligand-antibody-antibody-enzyme complex retained by said membrane with an aqueous wash solution to separate uncomplexed materials from said complex, and
   G. adding a reagent composition capable of providing a detectable species in the presence of said enzyme, and determining the presence of said species as an indication of the presence of antibodies specific to said ligand in said specimen.

2. The method of claim 1 carried out using a disposable test device having said microporous filtration membrane mounted therein.

3. The method of claim 1 wherein said ligand is insolubilized as part of an immunological reagent comprising polymeric particles having an average particle size greater than about 0.1 micrometers, and composed of one or more polymers prepared from one or more ethylenically unsaturated polymerizable monomers at least one of which has active halo atoms or activated 2-substituted ethylsulfonyl or vinylsulfonyl groups.

4. The method of claim 1 wherein washing is carried out with an aqueous wash composition buffered at a pH of from about 5 to about 10 and comprising a water-miscible polar organic solvent, an alkali metal or ammonium salt present in an amount sufficient to provide an ionic strength of at least about 0.25 and a surfactant.

5. The method of claim 1 wherein washing is carried out with an aqueous wash composition buffered to a pH of from about 5 to about 10 and comprising at least about 1.5 weight percent of a surfactant comprising a lower alcohol sulfate anion having from 6 to 10 carbon atoms and an alkali metal or ammonium cation.

6. The method of claim 1 wherein said insoluble ligand-antibody complex is not separated from uncomplexed materials on said membrane prior to addition of said enzyme-labeled antibodies.

7. The method of claim 1 for the determination of viral antibodies.

8. The method of claim 7 for the determination of retroviral antibodies.

9. The method of claim 8 for the determination of HIV-I antibodies.

10. A diagnostic kit useful for the determination of antibodies in a biological specimen, said kit comprising:
    (a) a diluent composition buffered to a pH of from about 6 to about 10 and comprising:
       an unmodified or underivatized protein or carbohydrate selected from the group consisting of gum arabic, dextran, gelatin argot, and human or animal serum or a component thereof,
       a surfactant, and
       a water-soluble, negatively-charged protein or carbohydrate,
    (b) an aqueous wash composition buffered at a pH of from about 5 to about 10 and comprising a surfactant, and
    (c) an immunological reagent comprising water-insoluble polymeric particles to which are bound ligand specific to said antibodies.

11. The kit of claim 10 further comprising a disposable test device comprising a filtration membrane.

12. The kit of claim 10 further comprising enzyme-labeled antibodies specific to said antibodies which are specific to said ligand, and a reagent composition capable of providing a detectable species in the presence of said enzyme.

13. The kit of claim 10 wherein said reagent is immobilized in a disposable test device.

* * * * *